United States Patent [19]
Jakkula et al.

[11] Patent Number: 6,127,589
[45] Date of Patent: Oct. 3, 2000

[54] PROCESS OF PRODUCING 2,6-DIMETHYLNAPHTHALENE BY DEHYDROCYCLIZING 1-(P-TOLYL)-2-METHYLBUTANE AND/OR 1-(P-TOLY)-2-METHYLBUTENE USING A REDUCED VANADIUM CATALYST

[75] Inventors: Juha Jakkula, Kerava; Vesa Niemi, Porvoo; Kari Vahteristo; Kari-Matti Sahala, both of Lappeenranta, all of Finland

[73] Assignee: Optatech Oy, Espoo, Finland

[21] Appl. No.: 09/125,109

[22] PCT Filed: Feb. 14, 1997

[86] PCT No.: PCT/FI97/00095

§ 371 Date: Sep. 15, 1998

§ 102(e) Date: Sep. 15, 1998

[87] PCT Pub. No.: WO97/30012

PCT Pub. Date: Aug. 21, 1997

[30] Foreign Application Priority Data

Feb. 16, 1996 [FI] Finland ................................. 960710

[51] Int. Cl.[7] .................. C07C 15/00; C07C 5/00; C07C 6/00

[52] U.S. Cl. ............................................. 585/411; 585/410

[58] Field of Search ........................................ 585/410, 411

[56] References Cited

U.S. PATENT DOCUMENTS

| | | | |
|---|---|---|---|
| 3,962,139 | 6/1976 | Van De Moessdijk et al. | 252/463 |
| 5,157,182 | 10/1992 | McMahon et al. | 585/411 |
| 5,382,733 | 1/1995 | Otake et al. | 585/407 |

FOREIGN PATENT DOCUMENTS

| | | |
|---|---|---|
| 0430714 | 6/1991 | European Pat. Off. . |
| 0557722 | 9/1993 | European Pat. Off. . |

*Primary Examiner*—Walter D. Griffin
*Assistant Examiner*—Thaun D. Dang
*Attorney, Agent, or Firm*—Oblon, Spivak, McClelland, Maier & Neustadt, P.C.

[57] ABSTRACT

The invention concerns a preparation process for 2,6-dimethylnaphthalene in which 1-(p-tolyl)-2-methylbutane and/or 1-(p-tolyl)-2-methylbutene are dehydrocyclisized using a reduced vanadium catalyst. 2,6-dimethylnaphthalene can be used as starting material when manufacturing poly-ethylenenaphthalate. The conversion of this method is good and the selectivity of 2,6-dimethylnaphthalene can be improved by reducing the catalyst.

13 Claims, No Drawings

PROCESS OF PRODUCING 2,6-DIMETHYLNAPHTHALENE BY DEHYDROCYCLIZING 1-(P-TOLYL)-2-METHYLBUTANE AND/OR 1-(P-TOLY)-2-METHYLBUTENE USING A REDUCED VANADIUM CATALYST

FIELD OF THE TECHNOLOGY

The invention concerns a process for the preparation of 2,6-dimethylnaphthalene in which 1-p-tolyl)-2-methylbutane and/or 1-(p-tolyl)-2-methylbutene are dehydro-cyclisized using a catalyst. 2,6-dimethylnaphthalene can be used as a starting material when making polyethylenenaphthalate.

BACKGROUND OF THE TECHNOLOGY

Polyethylenenaphthalate has very good stress- and heat-resistance. Its known preparation processes, however, have not been industrially profitable.

Polyethylenenaphthalate can be made from 2,6-naphthalenedicarboxylic acid which in turn can be made from 2,6 dimethylnaphthalene. Nowadays 2,6 dimethyl-naplthalene is separated from tar. However, in this way only small amounts can be obtained. Furthermore, the separation and purification are troublesome.

It has also been suggested that 2,6-dimethylnaphthalene is made from 1-(p-tolyl)-2-methylbutane and/or 1-(p-tolyl)-2-methylbutene by cyclization using different catalysts. The problem has especially been that in the reaction one obtains big amounts of different isomers, which are difficult to separate. Furthermore, the starting material easily polymerizes and degrades.

For instance, in the publication GB 1448136 there has been described the preparation of 1-tolyl)-2-methylbutane and/or 1(p-tolyl)-2-methylbutene using a $Cr_2O_3/Al_2O_3$-catalyst which has been poisoned by potassium. In the publication EP 430714 a catalyst composed of lead- and/or indium-oxide together with aluminium-oxide has been proposed.

A General Description of the Invention

Now a process according to claim 1 has been invented. Some advantageous applications of the invention are presented in the other claims.

According to the invention, 2,6-dimethylnaphthalene is made from 1-(p-tolyl)-2-methylbutane and/or 1-(p-tolyl)-2-methylbutene using a reduced vanadium catalyst. For instance, the conversion of the process is good compared to chromium catalysts, and especially the selectivity of 2,6-dimethylnaphthalene can be improved by reduction of the catalyst. Also the environmental risks for the vanadium catalyst can be considered smaller than for the chromium- and lead-catalysts.

A Detailed Description of the Invention

The vanadium catalyst used in the invention can be made using any suitable method for applying vanadium on a support. One can, for instance, use the methods of wet-or dry-impregnation or adsorption or precipitation. Among the dry-impregnation methods especially the co- and multi-impregnations provide good results both regarding the reaction and the phase transitions of the support material. After the impregnation, adsorption or precipitation the catalyst is dried at 120° C. and calcinated. The calcination is carried out in an oxidizing atmosphere, especially in air, in a temperature range of 300–800° C.

The preferred vanadium content is 1–15 wt-%, preferably 2–5 wt-%, calculated as vanadium per total weight of the catalyst. In the preparation the preferred vanadium source can be a water soluble vanadium compound like ammonium vanadate. The solubility of ammonium vanadate can be improved by adding oxalic acid to the impregnation solution.

The catalyst can also contain one or several modifying components. Suitable modifying components are especially the earth alkali metals, most favourably calcium and strontium, as well as the metals of the elementary group IV A, for instance zirconium. Also the sources of the modifying components can be water soluble compounds like nitrates. The molar ratio of vanadium and the modifying component should be below 4 in the case of earth alkali metals and below 2 in the case of group IV A metals.

Any suitable material can be used as a support. For this purpose especially γ-, θ- or δ-aluminum oxides with a specific surface area of 50–400 $m^2/g$ are suitable. Before vanadium is impregnated on the support one can thermally stabilize the support. The modifying agent can be impregnated on the support before or after the stabilization.

The catalyst can be reduced in a suitable way especially by contacting it with a reducing gas phase like carbon monoxide or hydrogen. A suitable inert gas like nitrogen can be used for dilution. The contacting temperature can be for instance 400–700° C. and the contacting time 0.1–120 min. After the treatment the reducing gas is removed from the catalyst by flushing with a suitable gas like nitrogen.

The treatment of a vanadium oxide catalyst with carbon monoxide for ammoxidation of aromatic hydrocarbons is known from the publication U.S. Pat. No. 3,901,933. By this treatment one has tried to improve the activity of the catalyst in the reaction mentioned above.

The preparation of 2,6-dimethylnaphthalene according to the invention is done by contacting 1-(p-tolyl)-2-methylbutane and/or 1-(p-tolyl)-2-methylbutene under dehydrocyclization conditions with a catalyst which has been made as described above. As reaction temperature one can use 350–700° C., preferably 450–600° C. The reaction can be done at any pressure, for instance, in the range 0.1–5 bar. In addition to 1-(p-tolyl)-2-methylbutane and/or 1-(p-tolyl)-2-methylbutene one can feed to the reactor a diluent gas like, for instance, nitrogen or water vapour.

EXAMPLE 1

A carrier was made by crushing (0.5–1 mm) γ-aluminium oxide (surface area about 200 $m^2/g$, porosity 1.2 ml/g) and precalcinating at 750° C. for 16 h. Onto the carrier one co-impregnated a water solution of ammoniumvanadate [$NH_4VO_3$] and oxalic acid [$(COOH)_2 * 2H_2O$][the molar ratio of $NH_4VO_3$ and $(COOH)_2 * 2H_2O$ was 0.5] as well as water solution prepared from calcium nitrate [V/Ca molar ratio was 3]. The catalyst was aged for 1 h at room temperature, dried for 4 h at 120° C. and calcinated for 2 h at 700° C. (the temperature increase was 2° C./min). The vanadium content of the catalyst was 5 wt-%, and the aluminium oxide was still in the γ-form.

2.15 g (4 ml) of the catalyst prepared as presented above was put into a glass tube reactor. In the first experiment 97% 1-(p-tolyl)-2-methylbutane was fed to the reactor at an LHSV of 0.48 $h^{-1}$ using nitrogen as a carrier gas [$N_{2:1}$-(p-tolyl)-2-(methylbutane)=1.9]. The reaction took place under atmospheric pressure at 510° C. and the contact time was 3.9 s. In the second experiment the catalyst was reduced before the reaction with hydrogen at 650° C. (20 ml/min, 15 min)

and in the third experiment with carbon monoxide at 650° C. (20 ml/min, 15 min). After the reduction and before starting the reaction the catalyst was flushed with nitrogen. For each experiment the sample was taken 60 min after starting the experiment. The results are presented in the table below.

|  | V/Ca/Al$_2$O$_3$ | V/Ca/Al$_2$O$_3$ H$_2$-red. | V/Ca/Al$_2$O$_3$ CO-red. |
|---|---|---|---|
| Conversion (C) | 69.4 | 65.8 | 63.6 |
| C$_6$–C$_{11}$ | 42.2 | 45.5 | 42.0 |
| 2-methylnaphthalene | 0.7 | 0.7 | 0.9 |
| 1-(p-tolyl)-2-methylbutenes | 10.2 | 13.2 | 14.1 |
| C$_{12}$-alkyl-indanes | 1.0 | 0.9 | 0.9 |
| C$_{12}$-alkyl-indenes | 9.8 | 7.4 | 7.3 |
| Dimethylnaphthalenes | 29.7 | 26.0 | 30.1 |
| (as 2,6-dimethylnaphthalene) | 26.2 | 24.0 | 27.7 |

According to the results, the portion of dimethylnaphthalenes which is as 2,6-dimethylnaphthalene increases when the catalyst has been pre-reduced. Furthermore, the reduced catalysts achieve a better selectivity level more rapidly after starting the experiment as compared to a non-reduced catalyst.

EXAMPLE 2

Onto the pre-calcinated support made in Example 1 zirconium nitrate (starting material ZrO(NO$_3$)$_2$* H$_2$O) was dry-impregnated. Then it was aged for 1 h and dried at 120° C. for 4 h after which it was impregnated with an ammonium vanadate-oxalic acid-solution according to Example 1. Then it was aged for 1 h and dried and calcinated as in Example 1. The vanadium content of the catalyst was 2.6 wt-%, the V/Zr-molar ratio 1 and the aluminium oxide was in the γ-form. The catalyst can be reduced and used in the reaction as in Example 1.

What is claimed is:

1. Process for preparing 2,6-dimethylnaphthalene, comprising dehydrocyclizing 1-(p-tolyl)-2-methylbutane and/or 1-(p-tolyl)-2-methylbutene using a reduced vanadium catalyst.

2. Process according to claim 1, wherein the catalyst is attached to a solid support.

3. Process according to claim 1, wherein the vanadium concentration in the catalyst is 1–15 wt-%.

4. Process according claim 1, wherein the catalyst additionally contains a modifier.

5. Process according to claim 4, wherein the modifier is calcium.

6. Process according to claim 1, wherein the catalyst is reduced using a reducing gas.

7. Process according to claim 6, wherein the catalyst has been reduced in a carbon monoxide containing atmosphere.

8. Process according to claim 6, wherein the catalyst has been reduced by hydrogen.

9. Process according to claim 6, wherein the catalyst has been reduced by contacting it with a reducing gas at 450–700° C. for 0.1–120 min.

10. Process according to claim 2, wherein the solid support is γ, θ- or δ-aluminium oxide.

11. Process according to claim 4, wherein the modifier is an earth alkali metal.

12. Process according to claim 4, wherein the modifier is a group IVA metal.

13. Process according to claim 12, wherein the group IVA metal is zirconium.

* * * * *

UNITED STATES PATENT AND TRADEMARK OFFICE
CERTIFICATE OF CORRECTION

PATENT NO. : 6,127,589

DATED : October 3, 2000

INVENTOR(S): Juha JAKKULA, et al.

It is certified that an error appears in the above-identified patent and that said Letters Patent is hereby corrected as shown below:

On the Title page, Item [54], and Column 1, the Title is spelled incorrectly. The Title should read as follows:

--[54]  PROCESS FOR PRODUCING 2,6-DIMETHYLNAPHTHALENE BY DEHYDROCYCLIZING 1-(P-TOLYL)-2-METHYLBUTANE AND/OR 1-(P-TOLYL)-2-METHYLBUTENE USING A REDUCED VANADIUM CATALYST  --

Signed and Sealed this

Eighth Day of May, 2001

Attest:

NICHOLAS P. GODICI

Attesting Officer

Acting Director of the United States Patent and Trademark Office